United States Patent [19]
Polanco

[11] 3,938,252
[45] Feb. 17, 1976

[54] RELATOR FOR DENTAL CASTS
[76] Inventor: Julio R. Polanco, 1 E. Harriet Ave., Palisades Park, N.J. 07650
[22] Filed: Aug. 9, 1974
[21] Appl. No.: 496,175

[52] U.S. Cl. .................................................. 32/32
[51] Int. Cl.² ....................................... A61C 11/00
[58] Field of Search ............................. 32/32, 40 R

[56] References Cited
UNITED STATES PATENTS
3,043,009  7/1962  Whitman ............................. 32/32

*Primary Examiner*—Robert Peshock
*Attorney, Agent, or Firm*—Samuelson & Jacob

[57] ABSTRACT

A relator for use in mounting complementary maxillary and mandibular dental casts in desired occluded arrangement within a pair of shell-like bases includes a locator having edges, each with a profile configuration complementary to a predetermined profile configuration on a complementary shell-like base, and a platform between the edges, the edges being spaced from one another a distance corresponding to the location of the shell-like bases when the bases are engaged with the edges of the locator and the dental casts are resting upon the platform in the desired occluded arrangement.

12 Claims, 12 Drawing Figures

RELATOR FOR DENTAL CASTS

The present invention relates generally to mounting dental casts and pertains, more specifically, to apparatus for mounting complementary maxillary and mandibular dental casts for display in desired occluded arrangement.

The making and preparation of dental models is a necessary part of dental and orthodontic procedure where a practitioner wishes to display to a patient the appearance of treated teeth before and after treatment.

In order to facilitate the mounting of dental casts for such models, preformed bases have been developed which enable dental casts to be mounted properly and in appropriate occlusal alignment with the respective bases in less time and with less difficulty than that encountered with previous equipment and procedures which required difficult, tedious, expensive and time-consuming molding and finishing operations. However, the use of such preformed bases in making models requires that auxiliary apparatus, in the form of a positioner and a relator, be used to assist in mounting and properly aligning the dental casts relative to the preformed bases. These preformed bases, the positioner and the relator are illustrated in U.S. Pat. No. 3,043,009.

In my earlier co-pending patent application, Ser. No. 415,422, filed Nov. 13, 1973, now U.S. Pat. No. 3,882,602 I described apparatus and method in which the model making procedure was further simplified and shortened by eliminating entirely the requirement for auxiliary apparatus in the form of the earlier positioner and relator in attaining the desired result. The apparatus described in my earlier application included a pair of complementary preformed bases having a construction different from the preformed bases of U.S. Pat. No. 3,043,009.

I now find that many preformed bases constructed in accordance with U.S. Pat. No. 3,043,009 are already in the field and that it would be advantageous if at least some of the procedures set forth in my earlier U.S. Pat. No. 3,882,602 could be applied to model making utilizing the preformed bases of patent number 3,043,009, but eliminating at least some of the auxiliary apparatus disclosed in that patent, along with some of the more time-consuming steps of the procedure.

It is therefore an object of the invention to provide apparatus which enables complementary maxillary and mandibular dental casts to be mounted in already available preformed bases for display in proper occluded arrangement, without requiring all of the special auxiliary apparatus and all of the procedural steps required heretofore with such preformed bases.

Another object of the invention is to provide a relator which enables already available preformed bases, or bases constructed in a similar manner, to be employed in the preparation of dental models utilizing a simplified procedure and less auxiliary apparatus than required heretofore.

Still another object of the invention is to provide a locator member which adapts a currently available relator for enabling already available preformed bases, or bases constructed in a similar manner, to be used in dental model making employing a simplified procedure which eliminates the need for a positioner.

A further object of the invention is to provide apparatus which enables a simplified, efficient and shorter method for the mounting of complementary dental casts in preformed bases.

A still further object of the invention is to provide apparatus of the type described which is relatively simple in construction and inexpensive to manufacture, while being easily used by the practitioner.

The above objects, as well as still further objects and advantages, are attained by the invention which may be described briefly as a relator for use in mounting complementary maxillary and mandibular dental casts in desired occluded arrangement within a pair of shell-like bases, each base having a bottom, side walls, an anterior wall and a posterior wall all integral with the bottom and extending therefrom to establish a cavity, the posterior wall having an external planar surface, an opposite internal surface and a peripheral edge surface between the external and internal surfaces, the peripheral edge surfaces each having a predetermined profile configuration, the relator comprising a base plate, a planar surface on the base plate, the planar surface extending longitudinally between opposite ends and laterally between opposite sides, locator means on the base plate raised from the planar surface, the locator means including a first altitudinal edge adjacent one of the opposite ends and a second altitudinal edge adjacent the other of the opposite ends, the first altitudinal edge having a profile configuration at least portions of which are complementary to the predetermined profile configuration of the peripheral edge surface of one of the bases, the second altitudinal edge having a profile configuration at least portions of which are complementary to the predetermined profile configuration of the peripheral edge surface of the other of the bases, the altitudinal edges being spaced apart from one another longitudinally a distance corresponding to the location of the shell-like bases when the peripheral edge surfaces of the bases are engaged with the corresponding altitudinal edges of the locator means and the dental casts are in the desired occluded arrangement.

The invention will be more fully understood, while still further objects and advantages thereof will become apparent, by reference to the following detailed description of preferred embodiments of the invention illustrated in the accompanying drawing, in which.

Figure 1:
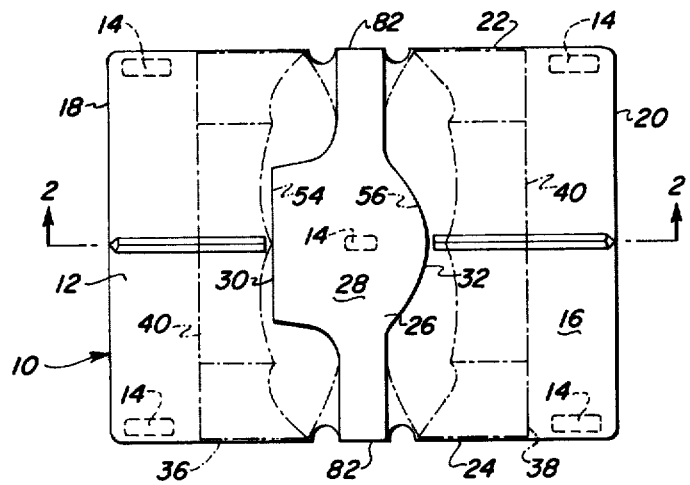
FIG. 1 is a top plan view of a relator constructed in accordance with the invention, with the addition of preformed bases illustrated in phantom.
Figure 2:
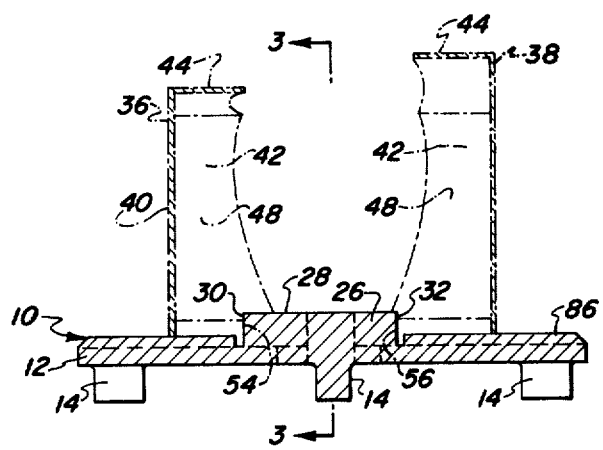
FIG. 2 is a longitudinal cross-sectional view taken along line 2—2 of FIG. 1.
Figure 3:
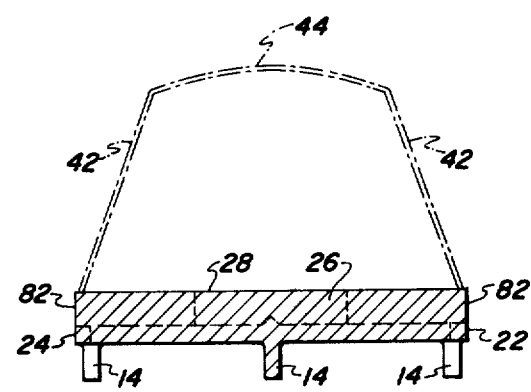
FIG. 3 is a cross-sectional view taken along line 3—3 of FIG. 2.
Figure 4:
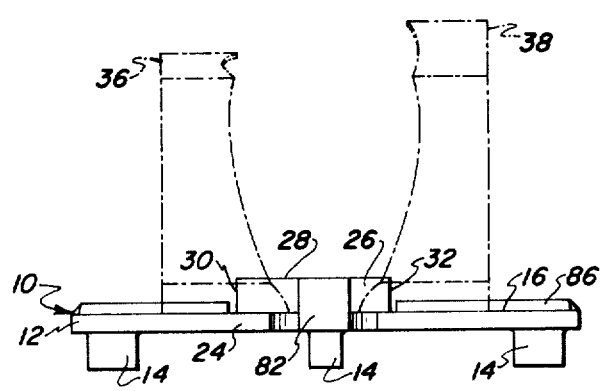
FIG. 4 is a side elevational view of the relator with preformed bases illustrated in phantom.
Figure 5:
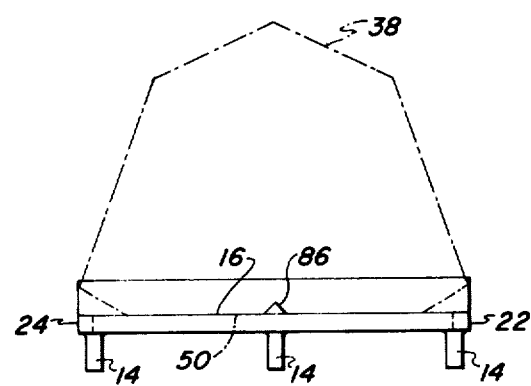
FIG. 5 is an end elevational view of the relator as illustrated in FIG. 4.

Referring now to the drawing, and especially to FIGS. 1 through 5 thereof, apparatus constructed in accordance with the invention is illustrated in the form of relator 10 which is seen to have a base plate 12 with depending feet 14 for supporting the base plate upon a counter top, a table top or the like.

Base plate 12 has an upper, planar surface 16 extending longitudinally between opposite ends 18 and 20 of the base plate and laterally between opposite sides 22 and 24. Intermediate the opposite ends 18 and 20 are locator means illustrated in the form of a platform 26 raised from the planar surface 16 and including a planar surface 28 extending parallel to surface 16 longitudinally between a first edge 30, extending in an altitudinal direction, i.e., generally perpendicular to the longitudinal and lateral directions, and a second altitudinal edge 32 and laterally between the opposite sides 22 and 24. Each altitudinal edge 30 and 32 has a particular profile configuration, as viewed in FIG. 1, for purposes which will be described below.

Relator 10 is to be used in mounting complementary maxillary and mandibular casts in desired occluded arrangement within a pair of shell-like preformed bases, such as those illustrated in U.S. Pat. No. 3,043,009. The preformed bases are shown in phantom in FIGS. 1 through 5 and can be seen in full lines in FIGS. 6 and 7, as maxillary base 36 and mandibular base 38. Each base 36 and 38 has a bottom 40, side walls 42, an anterior wall 44 and a posterior wall 46, all integral with the bottom and extending therefrom to establish a cavity 48 within each base. The posterior wall 46 of each base has an external planar surface 50 and an opposite internal surface 52.

Between the external planar surface 50 and opposite internal surface 52 of posterior wall 46 of base 36 is a peripheral edge surface 54 having a first predetermined profile configuration. Between the external surface 50 and opposite internal surface 52 of posterior wall 46 of base 38 is a peripheral edge surface 56 having a second predetermined profile configuration. The profile configuration of altitudinal edge 30 is generally complementary to the predetermined profile configuration of edge surface 54 of maxillary base 36, while the profile configuration of altitudinal edge 32 is generally complementary to the predetermined profile configuration of the edge surface 56 of mandibular base 38.

Figure 6:
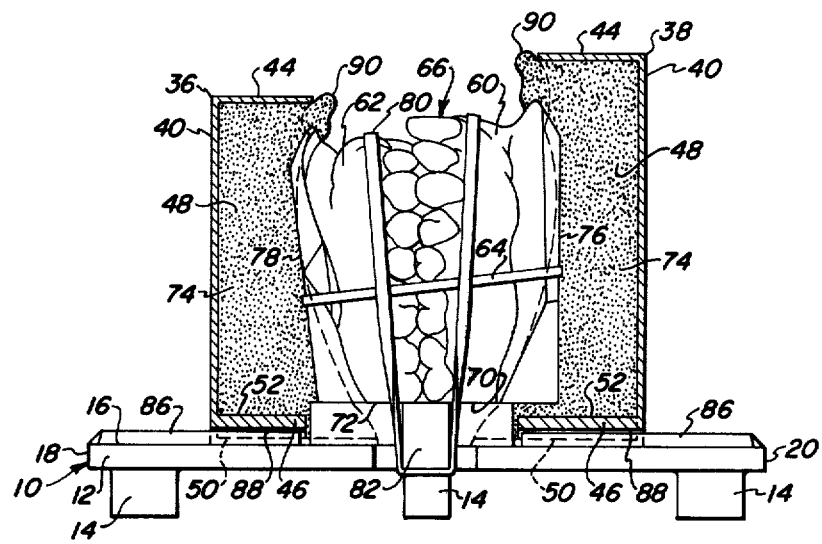
FIG. 6 is an enlarged side elevational view showing the relator in use, with complementary dental casts and preformed bases, the bases being illustrated in cross-section.
Figure 7:
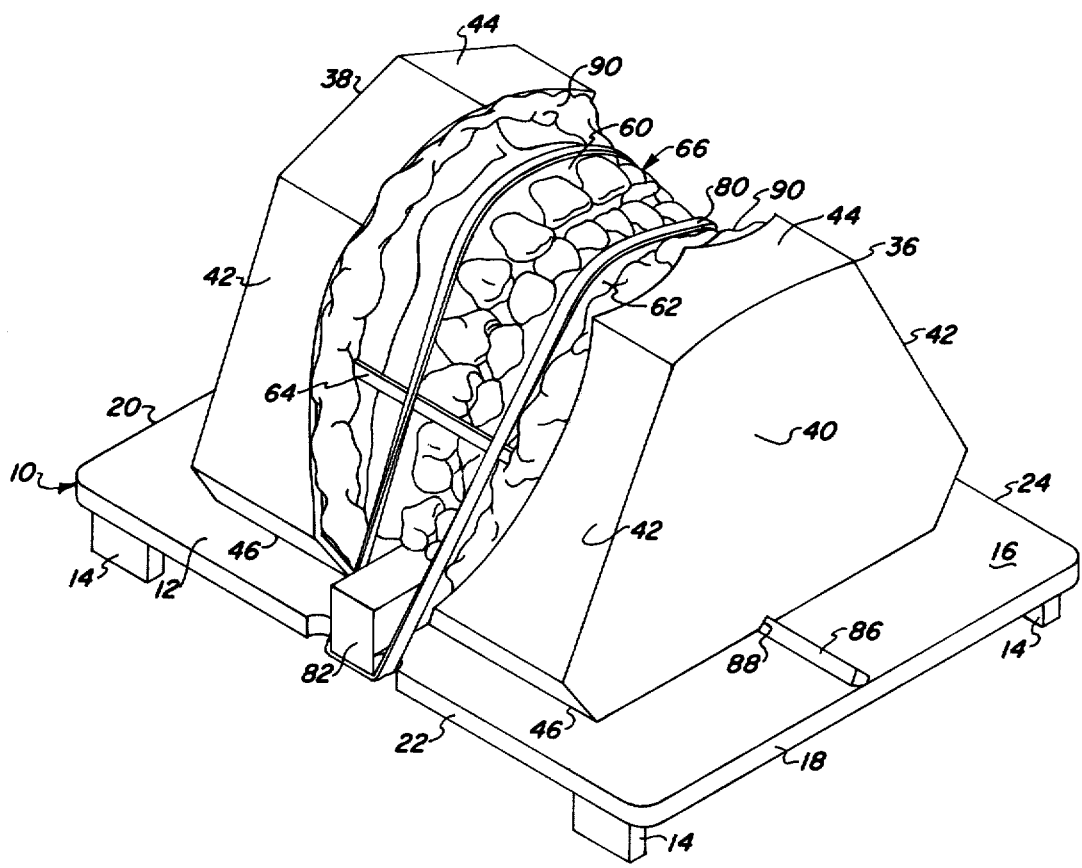
FIG. 7 is an enlarged perspective view of the relator in use, with complementary dental casts and preformed bases.
Figure 8:
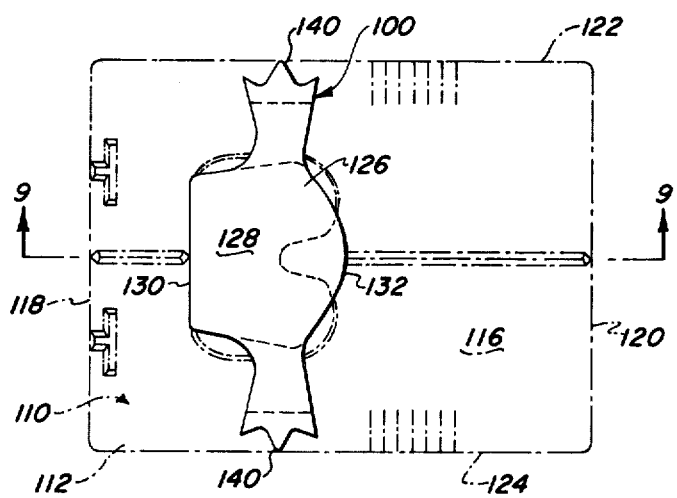
FIG. 8 is a top plan view of a locator member constructed in accordance with the invention and in place in an already available relator, illustrated in phantom.
Figure 9:
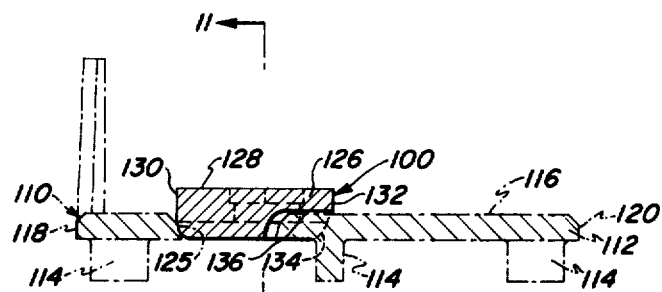
FIG. 9 is a longitudinal cross-sectional view taken along line 9—9 of FIG. 8.
Figure 10:
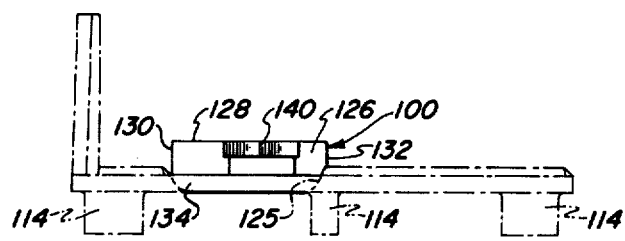
FIG. 10 is a side elevational view of the locator member in place in an already available relator, illustrated in phantom.
Figures 11, 12:
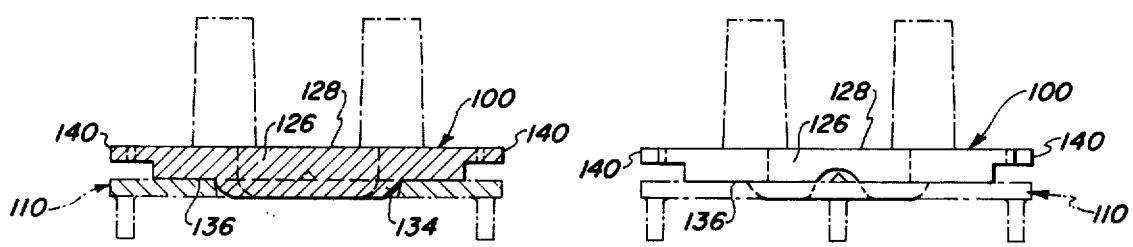
FIG. 11 is a cross-sectional view taken along line 11—11 of FIG. 8.
FIG. 12 is an end elevational view of the locator member in place in the phantom relator.

Turning now to FIGS. 6 and 7, as well as to FIGS. 1 through 5, dental casts 60 and 62, which have been fabricated of plaster in a well-known manner, are first assembled and then temporarily secured together in the desired occluded arrangement as by the use of a rubber band 64 which holds the dental casts 60 and 62 in an assembly 66. The assembled dental casts are then provided each with a posterior locating surface 70 and 72, respectively, by grinding, cutting or otherwise removing portions of the dental casts to establish the required locating surface configuration. In this instance, locating surfaces 70 and 72 are planar surfaces which match the planar configuration of planar surface 28 of platform 26.

An adhesive medium 74 is placed in each cavity 48 of the preformed bases 36 and 38 and, if so desired, upon the outside faces 76 and 78 of the dental casts 60 and 62. The bases 36 and 38 are then placed upon the planar surface 16 of the base plate 12, which receives the complementary external planar surface 50 of each preformed base, with each preformed base being in an initial position shown in phantom in FIG. 6, and the locating surfaces 70 and 72 of the occluded assembly 66 are placed upon the complementary planar surface 28 of platform 26. Preferably, a second rubber band 80 is passed over the assembly 66 and around lateral projections 82 located at the opposite sides 22 and 24 to secure the assembly 66 upon the platform 26. The bases 36 and 38 are then moved toward one another by sliding the bases along the planar surface 16 in the directions indicated by the arrows in FIG. 6, thereby engaging the edge surfaces 54 and 56 with the corresponding complementary altitudinal edges 30 and 32 of the platform 26. Once the edge surfaces 54 and 56 are fully seated against the altitudinal edges 30 and 32, the bases are in a prescribed position, as seen in full lines in FIG. 6, wherein the proper relative alignment and location is established between the bases.

Proper longitudinal alignment of the bases is further facilitated by alignment means shown in the form of longitudinal track 86, which is integral with the base plate 12, and a complementary groove 88 in the posterior wall 46 of each base. Although only one track 86 is illustrated for each base and is located centrally between the opposite sides 22 and 24, more than one track may be placed intermediate the sides 22 and 24, together with complementary grooves in each base to further enhance longitudinal alignment. The dental casts 60 and 62, already assembled in the desired occluded arrangement, are thus located relative to the bases by the engagement of the assembly 66 with the planar surface 28 of platform 26 and the engagement of the edge surfaces 54 and 56 with the altitudinal edges 30 and 32 of the platform.

The adhesive medium 74 which is placed between the confronting portions of the occluded assembly 66 and the bases 36 and 38 simultaneously adheres each dental cast to its respective base. Thus, the dental casts are located in the desired occluded arrangement when the bases are in the prescribed relative position dictated by the platform. As best seen in FIGS. 6 and 7, excess adhesive medium is exuded from between the confronting portions of the occluded assembly 66 and the bases 36 and 38 at 90 as the bases are moved toward one another to join the bases with the dental casts. The exuded adhesive medium may be trimmed, after hardening, to finish the model. At the same time, the rubber band 80 may be trimmed so that the upper and lower halves of the completed model may be parted.

Since the dental casts are fabricated of plaster, the adhesive medium 74 preferably is plaster. The bases 36 and 38 are usually fabricated of a synthetic resin material, but they too may be made of plaster so that all portions of the model may be finished with the same techniques and the resulting model will have a uniform, aesthetically pleasing appearance.

It will be apparent, then, that relator 10 enables the shell-like bases 36 and 38 to be utilized in a procedure much like that described in my earlier application Ser. No. 415,422, thus accomplishing a saving in the number of steps required and the number of pieces of auxiliary equipment required, with concomitant savings in time and expense. The procedure described in U.S. Pat. No. 3,043,009 utilizing the positioner described therein becomes unnecessary, but the bases themselves need not be altered.

Referring now to FIGS. 8 through 12, there is illustrated locator means in the form of locator member 100 adapted for use with the relator described in U.S. Pat. No. 3,043,009, to convert that relator for use in a procedure similar to that described above in connection with relator 10.

A relator constructed in accordance with the disclosure of U.S. Pat. No. 3,043,009 is illustrated in phantom at 110 in FIGS. 8 through 12 and is seen to include a base plate 112 with depending feet 114 and an upper planar surface 116 extending longitudinally between opposite ends 118 and 120 and laterally between opposite sides 122 and 124. The base plate 112 includes an opening 125 which passes through the base plate.

Locator member 100 has a platform 126 which includes a planar surface 128 extending longitudinally between opposite edges 130 and 132. As in the relator 10 described above, the edges 130 and 132 each have a profile contour configuration complementary to the predetermined profile configuration of the peripheral edge surface of a corresponding shell-like base which is to be placed upon the planar surface 116 of base plate 112.

Positioning means are shown in the form of a depending plug portion 134 which has a configuration including portions complementary to the configuration of opening 125 so as to be received therein. Placement of the plug portion 134 within opening 125 will bring shoulders 136 of the locator member 100 into engagement with the surface 116 of base plate 112, while the complementary portions of plug portion 134 locate the edges 130 and 132 relative to the base plate 112. In this manner, platform 126 provides the appropriate raised surface 128 and opposite edges 130 and 132 to enable the assembled locator member 100 and relator 110 to function in a manner similar to relator 10.

A projection 140 extends laterally at each side of the locator member 100, projections 140 providing securing means by which an assembly of dental casts, such as assembly 66 described above, may be secured upon platform 126 in the manner described above.

Thus, a relatively simple locator member 100 serves as an adaptor enabling an already available relator to be used in a simplified, time and equipment saving manner.

It is to be understood that the above detailed description of preferred embodiments of the invention is provided by way of example only. Various details of design and construction may be modified without departing from the true spirit and scope of the invention as set forth in the appended claims.

The embodiments of the invention in which an exclusive property or privilege is claimed are defined as follows:

1. A relator for use in mounting complementary maxillary and mandibular dental casts in desired occluded arrangement within a pair of shell-like bases, each base having a bottom, side walls, an anterior wall and a posterior wall all integral with the bottom and extending therefrom to establish a cavity, said posterior wall having an external planar surface, an opposite internal surface and a peripheral edge surface between said external and internal surfaces, the peripheral edge surfaces each having a predetermined profile configuration, said relator comprising:
   a base plate;
   a planar surface on the base plate, said planar surface extending longitudinally between opposite ends and laterally between opposite sides;
   locator means on the base plate raised from the planar surface, said locator means including a first altitudinal edge adjacent one of said opposite ends and a second altitudinal edge adjacent the other of said opposite ends;
   the first altitudinal edge having a profile configuration at least portions of which are complementary to the predetermined profile configuration of the peripheral edge surface of one of the bases;
   the second altitudinal edge having a profile configuration at least portions of which are complementary to the predetermined profile configuration of the peripheral edge surface of the other of the bases; and
   said altitudinal edges being spaced apart from one another longitudinally a distance corresponding to the location of the shell-like bases when the peripheral edge surfaces of the bases are engaged with the corresponding altitudinal edges of the locator means and the dental casts are in said desired occluded arrangement.

2. The invention of claim 1 wherein said locator means include a platform raised from the planar surface and extending longitudinally between the first and second altitudinal edges and laterally between the opposite sides of the planar surface for supporting the occluded dental casts.

3. The invention of claim 2 wherein the platform includes a planar surface parallel to the planar surface of the base plate.

4. The invention of claim 2 wherein the external surface of the posterior wall of each shell-like base includes first alignment means for lateral alignment of the shell-like bases and the base plate includes second alignment means complementary to the first alignment means, located laterally intermediate the opposite sides of the planar surface thereof and extending longitudinally therealong for engaging the first alignment means and aligning the shell-like bases relative to one another upon the base plate.

5. The invention of claim 4 wherein the first alignment means include at least one groove and the second alignment means include at least one longitudinal track complementary to said groove.

6. The invention of claim 2 wherein the base plate includes securing means at each side of the planar surface for enabling securement of the occluded dental casts in place upon said platform.

7. The invention of claim 6 wherein the occluded dental casts are to be secured upon the platform with an elastic band and said securing means include a lateral projection at each side of the planar surface around which projections said elastic band may be placed.

8. A locator member for use in a relator in mounting complementary maxillary and mandibular dental casts in desired occluded arrangement within a pair of shell-like bases, each base having a bottom, side walls, an anterior wall and a posterior wall all integral with the bottom and extending therefrom to establish a cavity, said posterior wall having an external planar surface, an opposite internal surface and a peripheral edge surface between said external and internal surfaces, the peripheral edge surfaces each having a predetermined profile configuration, and said relator including a base plate, a planar surface on the base plate extending longitudinally between opposite ends and laterally between opposite sides and an opening in the planar surface of the base plate, said locator member comprising:
- a first edge having a profile configuration complementary to the predetermined profile configuration of the peripheral edge surface of one of the bases;
- a second edge having a profile configuration complementary to the predetermined profile configuration of the peripheral edge surface of the other of the bases;
- positioning means on the locator member, said positioning means depending relative to the said edges and receivable within the opening in the planar surface for positioning the locator member upon the planar surface with said first and second edges extending altitudinally relative to the planar surface; and
- said first and second edges being spaced apart from one another longitudinally a distance corresponding to the location of the shell-like bases when the peripheral edge surfaces of the bases are engaged with the corresponding edges of the locator member and the dental casts are in said desired occluded arrangement.

9. The invention of claim 8 wherein the locator member includes a platform extending longitudinally between said first and second edges for supporting the occluded dental casts.

10. The invention of claim 9 wherein the platform includes a planar surface.

11. The invention of claim 8 wherein the locator member has laterally opposite sides and includes securing means at each side for enabling securement of the occluded dental casts in place upon the platform.

12. The invention of claim 11 wherein the occluded dental casts are to be secured upon the platform with an elastic band and said securing means include a lateral projection at each side of the locator member around which projections said elastic band may be placed.

* * * * *